(12) United States Patent
Bombardelli

(10) Patent No.: US 7,597,915 B2
(45) Date of Patent: Oct. 6, 2009

(54) COMPOSITIONS FOR THE TREATMENT OF ATOPIC DERMATITIS, SKIN ALLERGIC CONDITIONS AND ACNE

(75) Inventor: Ezio Bombardelli, Groppello Cairoli (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/579,966

(22) PCT Filed: Nov. 8, 2004

(86) PCT No.: PCT/EP2004/012608

§ 371 (c)(1),
(2), (4) Date: May 23, 2006

(87) PCT Pub. No.: WO2005/053720

PCT Pub. Date: Jun. 16, 2005

(65) Prior Publication Data

US 2007/0071839 A1   Mar. 29, 2007

(30) Foreign Application Priority Data

Nov. 24, 2003   (IT)   .......................... MI2003A2286

(51) Int. Cl.
*A61K 36/16* (2006.01)
(52) U.S. Cl. ..................................... 424/752
(58) Field of Classification Search ........................ None
See application file for complete search history.

(56) References Cited

U.S. PATENT DOCUMENTS 5,578,312 A * 11/1996 Parrinello ................... 424/401
6,419,950 B2 * 7/2002 Bombardelli et al. ....... 424/452
7,008,627 B1 * 3/2006 Castelli et al. .............. 424/401
7,166,310 B2 * 1/2007 Koch et al. .................. 424/730
2004/0185123 A1   9/2004 Mazzio et al.
2006/0275246 A1 * 12/2006 Bombardelli et al. ......... 424/74

FOREIGN PATENT DOCUMENTS

EP   0 870 507   10/1998
RO   108642 B1 *   7/1994

OTHER PUBLICATIONS

Tamemoto et al, Sesquiterpenoids from the fruits of Ferula Kuhistanica and antibacterial activity of the consittuents of F. kuhistanica, Phytochemistry, vol. 5, Nov. 2001, pp. 763-767.*
Patent Abstracts of Japan, vol. 1998, No. 06, Apr. 30, 1998, & JP 10 053532 A (Ichimaru Pharcos Co Ltd), Feb. 24, 1998 abstract.
More D R et al:, "Herbal supplements and skin testing: The lack of effect of commonly used herbal suulemnts on histamine skin prck testing.", Allergy (Copenhagen), vol. 58, No. 6, Jun. 2003, pp. 492-494, XP009044026 ISSN: 0105-4538 the whole document.
Kiken David A et al:, "Contact dermatitis to botanical extracts.", American Journal of Contact Dermatitis: Official Journal of the American Contact Dermatitis Society, Sep. 2002, vol. 13, No. 3, Sep. 2002, pp. 148-152, XP009044006 ISSN: 1046-199X, the whole document.
Fugh-Berman A A:, "Herb-drug interactions", Lancet, XX, XX, vol. 355, No. 9198, Jan. 8, 2000, pp. 134-138, XP004262991, ISSN: 0140-6736, the whole document.

* cited by examiner

*Primary Examiner*—Christopher R. Tate
*Assistant Examiner*—Deborah A. Davis
(74) *Attorney, Agent, or Firm*—Young & Thompson

(57) ABSTRACT

The present invention relates to topical compositions containing: a) *Ginkgo biloba* terpenes; b) floroglucinols pure or in mixture thereof, extracted from *Humulus lupulus, Hypericum* sp and *Mirtus* sp; c) *Zanthoxylum bungeanum* or *Echinacea angustifolia* lipophilic extract; for the treatment of atopic dermatitis, skin allergic conditions and acne.

22 Claims, No Drawings

COMPOSITIONS FOR THE TREATMENT OF ATOPIC DERMATITIS, SKIN ALLERGIC CONDITIONS AND ACNE

The present invention relates to compositions containing medicinal plant extracts or purified or standardized fractions thereof, useful in the treatment of atopic dermatitis, skin allergic conditions and acne.

PRIOR ART

Atopic dermatites are characterized by persistent inflammatory conditions which may cause lacerations of the skin with possible infections. Inflammation is often accompanied by intense itching; the consequent scratching by the patient may further irritate the affected area.

Dermatites, which are also frequently referred to as eczema, are superficial skin inflammations, with acute or chronic course and variable clinical and histological manifestations, which affect an unnegligible percentage of population (2-3%).

The etiology of the various forms of dermatitis is still partly unclear, although the immune component is definitely one of the factors. The pathological manifestations are often alike, and are mainly characterized by the presence of papules, erythematous spots and vesicles, which can form plaques, edema, scaling-crusting lesions and the like. The most common dermatites comprise atopic dermatitis, contact allergies, contact dermatitis, stasis dermatitis, seborrheic dermatitis, lichen simplex and acne vulgaris.

The choice treatment consists in the use of corticosteroids, which involve well-known side effects (possible secondary infections, inefficacy after prolonged use, and the like).

DISCLOSURE OF THE INVENTION

It has now been found that compositions containing:
a) an extract, fraction thereof or pure compound with inflammatory action;
b) an extract, fraction thereof or pure compound, with antimicrobial and/or antifungal action; and
c) an extract, fraction thereof or pure compound, with anti-itching action;
exert immediate, beneficial effect to the patient and induce the fast remission of the pathological condition, even compared with known medicaments such as topical anti-inflammatories and steroids.

More precisely, the compositions of the invention comprise:
a) *Ginkgo biloba* terpenes;
b) floroglucinols, either pure or in mixture thereof, extracted from *Humulus lupulus, Hypericum* sp and *Mirtus* sp;
c) *Zanthoxylum bungeanum* or *Echinacea angustifolia* lipophilic extract.

According to the present invention, the *Ginkgo biloba* content can range from 0.1 to 2%; the floroglucinols content can range from 0.1 to 1%; and the *Zanthoxylum bungeanum* or *Echinacea angustifolia* lipophilic extract content can range from 0.01 to 0.5%.

According to the invention, *Ginkgo biloba* terpenes are present in the free form or preferably in the form of complex with natural or synthetic phospholipids. "*Ginkgo biloba* terpenes" herein means the terpenes, either pure or in a mixture wherein the total triterpenes content ranges from 60 to 100%, preferably 90%, the bilobalide content ranges from 20 to 70%, preferably 45%, and ginkgolides A, B, C and J total content ranges from 25 to 75%, preferably 50%.

*Ginkgo biloba* terpenes, in addition to the antinflammatory action, also exert antiallergic action, as observed in a number of models both in animals and humans, thereby reducing one of the symptoms involved, which keep irritation and the continuous recidivation. This antiallergic action makes said terpenes particularly useful when an immune factor is involved in the etiology.

Floroglucinols, either pure or in a mixture thereof extracted from *Humulus lupulus, Hypericum* sp and *Mirtus* sp., are active against anaerobic bacteria such as *Propionibacterium acnis* and the like and on *Candida albicans* strains, at concentrations of 0.5-4 µg/mL.

In particular, *Humulus lupulus* extracts are characterized by a floroglucinols content of 20 to 80%, preferably 60%. Among the extracts of *Hypericum* sp., particularly preferred is a *Hypericum perforatum* extract with a floroglucinols (adhyperforin/hyperforin) content ranging from 20 to 80%, preferably 60%. Among the extracts of *Mirtus* sp, particularly preferred is an extract of *Mirtus communis* leaves prepared by extraction with carbon dioxide under pressure ranging from 235 to 260 bars, at a temperature ranging from 40 to 60° C., preferably a 45° C. The resulting extract usually contains about 35% of mirtocumulone.

The compositions of the invention containing a *Zanthoxylum bungeanum* or *Echinacea angustifolia* lipophilic extract enriched in isobutylamides, active as topical analgesics inhibiting the nervous conduction proved particularly effective in the treatment of localized itching. Therefore, according to a preferred aspect, the compositions of the present invention will contain, as component c), a *Zanthoxylum bungeanum* or *Echinacea angustifolia* lipophilic extract enriched in isobutylamides. The *Zanthoxylum* extract can be prepared for example as disclosed in WO 00/02570, while the *Echinacea* extract can be prepared for example as disclosed in EP 0 464 298.

The compositions of the invention further containing natural compounds with estrogenic and/or antiandrogenic action proved particularly effective in the treatment of seborrheic dermatitis and acne. Therefore, according to a preferred aspect, the compositions of the present invention will contain, in addition to components a), b) and c) above, also natural compounds with estrogenic action, such as ferutinine and/or extracts of various *Ferula* species, and/or natural compounds with antiandrogenic action, such as lauric acid.

According to a further preferred aspect, the compositions of the present invention will contain *Oenothera biennis* oil as lipophilic excipient.

The present invention, therefore, relates to topical compositions for the treatment of atopic dermatitis, skin allergic conditions and acne, containing the combinations described above. Said compositions will be prepared according to conventional methods well known in the pharmaceutical technique, such as those described in "Remington's Pharmaceutical Handbook", Mack Publishing Co., N.Y., USA, together with suitable excipients commonly used in the art.

The examples reported hereinbelow further illustrate the invention.

EXAMPLE 1

| Oil-in-water emulsion | |
|---|---|
| *Ginkgo biloba* terpenes in form of phospholipid complexes | 0.5 g |
| *Humulus lupulus* extract (60% in floroglucinols) | 0.1 g |
| *Zanthoxylum bungeanum* extract | 0.05 g |
| *Oenothera biennis* oil | 5.0 g |
| Polyoxyethylene glycol-20 glyceryl stearate | 10.0 g |

-continued

| Oil-in-water emulsion | |
|---|---|
| $C_{10}$-$C_{18}$ triglycerides | 10.0 g |
| Glycerin | 5.0 g |
| Hydroxylated lanolin | 0.5 g |
| Hydroxyethyl cellulose | 0.5 g |
| Methyl and propyl paraben | 0.2 g |
| Tocopherol | 0.1 g |
| Purified water | q.s. to 100.0 g |

EXAMPLE 2

| Oil-in-water emulsion | |
|---|---|
| *Ginkgo biloba* terpenes in form of phospholipid complexes | 0.5 g |
| *Mirtus communis* lipophilic extract (35% in mirtocumulone) | 0.1 g |
| *Zanthoxylum bungeanum* extract | 0.05 g |
| *Oenothera biennis* oil | 5.0 g |
| Stearic acid | 10.0 g |
| Mineral oil | 6.0 g |
| White petrolatum | 6.0 g |
| Sorbitan monostearate | 2.0 g |
| Polyoxyethylene sorbitan monostearate | 1.0 g |
| Methyl and propyl paraben | 0.2 g |
| Purified water | q.s. to 100.0 g |

EXAMPLE 3

| Cream | |
|---|---|
| *Ginkgo biloba* terpenes in form of phospholipid complexes | 0.5 g |
| *Humulus lupulus* extract (60% in floroglucinols) | 0.1 g |
| *Echinacea angustifolia* extract | 0.05 g |
| *Oenothera biennis* oil | 5.0 g |
| Stearic acid | 12.0 g |
| Glycerin | 10.0 g |
| Cetostearyl alcohol | 2.0 g |
| Potassium hydroxide | 0.9 g |
| Methyl and propyl paraben | 0.2 g |
| Purified water | q.s. to 100.0 g |

EXAMPLE 4

| Cream | |
|---|---|
| *Ginkgo biloba* terpenes in form of phospholipid complexes | 0.5 g |
| *Hypericum perforatum* extract (60% in floroglucinols) | 0.1 g |
| *Echinacea angustifolia* extract | 0.05 g |
| *Oenothera biennis* oil | 5.0 g |
| Stearic acid | 12.0 g |
| Glycerin | 10.0 g |
| Cetostearyl alcohol | 2.0 g |
| Potassium hydroxide | 0.9 g |
| Methyl and propyl paraben | 0.2 g |
| Purified water | q.s. to 100.0 g |

EXAMPLE 5

| Cream | |
|---|---|
| *Ginkgo biloba* terpenes in form of phospholipid complexes | 0.5 g |
| *Humulus lupulus* extract (60% in floroglucinols) | 0.1 g |
| *Zanthoxylum bungeanum* extract | 0.05 g |
| *Oenothera biennis* oil | 5.0 g |
| Ferutinine | 0.3 g |
| Lauric acid | 0.3 g |
| Cetostearyl alcohol | 20.0 g |
| White petrolatum | 15.0 g |
| Propylene glycol | 10.0 g |
| Sodium lauryl sulfate | 1.0 g |
| Methyl and propyl paraben | 0.2 g |
| Purified water | q.s. to 100.0 g |

The invention claimed is:

1. A topical composition for the treatment of atopic dermatitis, skin allergic conditions or acne, comprising:
   effective amounts of:
   a) *Ginkgo biloba* terpenes, the terpenes being either pure or in a mixture having a total triterpenes content from 60 to 100%;
   b) floroglucinols, either pure or in mixture thereof, extracted from *Humulus lupulus, Hypericum* sp and *Mirtus* sp; and
   c) *Zanthoxylum bungeanum* or *Echinacea angustifolia* lipophilic extract.

2. The composition as claimed in claim 1, wherein the effective amounts are:
   a) 0.1 to 2% *Ginkgo biloba* terpenes;
   b) 0.1 to 1% floroglucinols, either pure or in a mixture thereof, extracted from *Humulus lupulus, Hypericum* sp and *Mirtus* sp; and
   c) 0.01 to 0.5% of *Zanthoxylum bungeanum* or *Echinacea angustifolia* lipophilic extract.

3. The composition as claimed in claim 1, wherein *Ginkgo biloba* terpenes are present in free form.

4. The composition as claimed in claim 1, wherein *Ginkgo biloba* terpenes are present in the form of a complex with natural or synthetic phospholipids.

5. The composition as claimed in claim 4, wherein the total triterpenes content ranges from 60 to 100%.

6. The composition as claimed in claim 5, wherein the total triterpenes content is 90%.

7. The composition as claimed in claim 4, wherein the terpenes comprises bilobalides and wherein the bilobalide content ranges from 20 to 70%.

8. The composition as claimed in claim 7, wherein the bilobalide content is 45%.

9. The composition as claimed in claim 4, wherein the terpenes comprises ginkolides A, B, C, and J, and wherein the total A, B, C and J ginkgolides content ranges from 25 to 75%.

10. The composition as claimed in claim 9, wherein the total A, B, C and J ginkgolides content is 50%.

11. The composition as claimed in claim 1, wherein the floroglucinols content of the *Humulus lupulus* extract ranges from 20 to 80%.

12. The composition as claimed in claim 11, wherein the floroglucinols content of the *Humulus lupulus* extract is 60%.

13. The composition as claimed in claim 1, wherein the *Hypericum* sp. extract is a *Hypericum perforatum* extract in which the floroglucinols content ranges from 20 to 80%.

14. The composition as claimed in claim 13, wherein the floroglucinols content of the *Hypericum perforatum* extract is 60%.

15. The composition as claimed in claim 1, wherein the extract of *Mirtus* sp is communis leaves and is prepared by extraction with carbon dioxide under conditions of pressure ranging from 235 to 260 bars and temperatures ranging from 40 to 60° C.

16. The composition as claimed in claim 15, wherein the *Mirtus* sp. extract is an extract of *Mirtus* communis leaves with a mirtocumulone content of 35%.

17. The composition as claimed in claim 1, wherein the *Zanthoxylum gungeanum* or *Echinacea angustifolia* lipophilic extract is enriched in isobutylamides.

18. The composition as claimed in claim 1, further comprising ferutinine.

19. The composition as claimed in claim 1, further comprising extracts of various *Ferula* species.

20. The composition as claimed in claim 1, further comprising lauric acid.

21. The composition as claimed in claim 1, further comprising *Oenothera biennis* oil as a lipophilic excipient.

22. A Method for the treatment of atopic dermatitis, skin allergic conditions or acne, which comprises administering to a patient in need thereof an effective amount of a medicament comprising:

a) *Ginkgo biloba* terpenes, the terpenes being either pure or in a mixture having a total triterpenes content from 60 to 100%;

b) floroglucinols pure or in a mixture thereof, extracted from *Humulus lupulus, Hypericum* sp and *Mirtus* sp; and c) *Zanthoxylum bungeanum* or *Echinacea angustifolia* lipophilic extract.

* * * * *